(12) United States Patent
Pan et al.

(10) Patent No.: US 9,662,026 B2
(45) Date of Patent: May 30, 2017

(54) THREE-DIMENSIONAL ELECTRODE AND A BIOLOGICAL PROBE COMPRISING THE SAME

(71) Applicant: National Tsing Hua University, Hsinchu (TW)

(72) Inventors: I-An Pan, Hsinchu (TW); Tri-Rung Yew, Hsinchu (TW); Hsin Chen, Hsinchu (TW); Yung-Jen Chuang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 176 days.

(21) Appl. No.: 14/622,409

(22) Filed: Feb. 13, 2015

(65) Prior Publication Data

US 2016/0120424 A1    May 5, 2016

(30) Foreign Application Priority Data

Oct. 31, 2014   (TW) .............................. 103137869 A

(51) Int. Cl.
| | |
|---|---|
| *A61B 5/04* | (2006.01) |
| *A61B 5/0408* | (2006.01) |
| *B82Y 30/00* | (2011.01) |
| *B82Y 15/00* | (2011.01) |

(52) U.S. Cl.
CPC ........ *A61B 5/04001* (2013.01); *A61B 5/0408* (2013.01); *A61B 2503/40* (2013.01); *A61B 2562/028* (2013.01); *A61B 2562/0214* (2013.01); *A61B 2562/0285* (2013.01); *A61B 2562/125* (2013.01); *A61B 2562/14* (2013.01); *B82Y 15/00* (2013.01); *B82Y 30/00* (2013.01)

(58) Field of Classification Search
CPC .................................................. A61B 5/04001
USPC .................................. 600/377, 378; 607/116
See application file for complete search history.

(56) References Cited

U.S. PATENT DOCUMENTS

| | | | |
|---|---|---|---|
| 7,551,951 B1* | 6/2009 | Osorio ................. | A61B 5/0478 600/378 |
| 8,774,890 B2* | 7/2014 | Ready ..................... | A61N 1/05 600/377 |
| 9,192,757 B2* | 11/2015 | Seymour .................. | A61N 1/05 |
| 2009/0004471 A1* | 1/2009 | Amthor .............. | A61B 5/04001 428/375 |
| 2013/0079615 A1* | 3/2013 | Yoon .................. | A61B 5/04001 600/377 |

(Continued)

OTHER PUBLICATIONS

Wang et al, "Neural Stimulation with a Carbon Nanotube . . . Array", Nano Letters, vol. 6, No. 9, pp. 2043-2048, 2006.*

*Primary Examiner* — Lee S Cohen
(74) *Attorney, Agent, or Firm* — Muncy, Geissler, Olds & Lowe, P.C.

(57) ABSTRACT

The present invention provides a three-dimensional electrode having high cell affinity and capacitive coupling, comprising a pillar portion and a spherical portion, wherein the diameter of the spherical portion is larger than that of the pillar portion, and the carbon nanotubes are coated on the spherical portion, and pillar portion and the spherical portion are made of material selected from metal materials. The present invention may be used for developing biological probes having high cell affinity and capacitive coupling so as to provide high accuracy for measurement of neural cells or electrocardiograms and prevent from distortion.

18 Claims, 7 Drawing Sheets

(56) References Cited

U.S. PATENT DOCUMENTS

2013/0085359 A1\* 4/2013 Yao ............... A61B 5/0478
   600/372
2014/0275934 A1\* 9/2014 Saini ............... A61B 5/6846
   600/393

\* cited by examiner

THREE-DIMENSIONAL ELECTRODE AND A BIOLOGICAL PROBE COMPRISING THE SAME

BACKGROUND OF THE INVENTION

1. Field of the Invention

The present invention relates to a three-dimensional electrode and a biological probe comprising the same, and particularly to a three-dimensional electrode with cell affinity and capacitive coupling and a biological probe comprising the same.

2. Description of the Prior Art

With the progress of science and technology, fields, detection items and precision requirements covered by the biomedical detection industry have been progressively increased, wherein the developments of the examination and treatment methods of many diseases associated with neurology, e.g., Alzheimer's disease, Parkinson's disease, sleep disorders, epilepsy, etc. must be carried out with high professional requirements and specific detection instruments. In general, the activities of the neural network are accomplished mainly by transmissions of electrical signals. Therefore, by detecting the transmission mechanisms and principles of the electrical signals of the neural system in the neural networks and the regulation of the electrical signals of the neural system by external factors, etc., we may have a further understanding about neurophysiology and related diseases.

Among them, the activities of the neural cells in the brain are usually accomplished by transmissions of electrical signals. Thus, in the related fields of the neurophysiological detection, neural probes are often used to stimulate or measure the neural cells, so as to understand the physiological function of the nerves. However, a variety of traditional developed microelectrode probes may have issues such as too large size, which may result in harming the cells, a high impedance, and insufficient cell affinity and so on. Therefore, the traditional microelectrode probes can not detect the activities of the neural cells reliably nor for a longer period.

To sum up the foregoing descriptions, developing an electrode probe, which has a sufficient cell affinity, a low impedance, and high capacitive coupling, is the most important goal for now.

SUMMARY OF THE INVENTION

An objective of the present invention is directed to providing a three-dimensional electrode with cell affinity and capacitive coupling and a biological probe comprising the same, which may help to achieved improved measurement accuracy for the neural cells or for the electrocardiogram, so as to avoid from a distorted result. Moreover, this three-dimensional electrode having carbon nanotubes may be provided with a larger contact area with the cells and provide preferred cell affinity, which may be effectively applied in the measurements of the electrical signals of the neural cells or the heart signals, so as to provide a preferred choice of a neural probes for related biomedical detection industry.

According to one embodiment of the present invention, a three-dimensional electrode with cell affinity and a capacitive coupling comprises a pillar portion and a spherical portion connected to each other, wherein a radius of the spherical portion is more than a radius of the pillar portion, and carbon nanotubes are formed on the spherical portion, wherein the pillar portion and the spherical portion is made of a metal material.

According to another embodiment of the present invention, a biological probe comprises: a base; an output contact disposed on the base; a three-dimensional electrode array disposed on the base, the three-dimensional electrode array being composed of the above-mentioned three-dimensional electrode with cell affinity and capacitive coupling; and an interconnect conductive layer disposed on the base and electrically connecting the output contact and the three-dimensional electrode array.

The purpose, technical content, characteristic and effect of the present invention will be easy to understand by reference to the following detailed descriptions, when taken in conjunction with the accompanying drawings and the particular embodiment.

Figure 6:
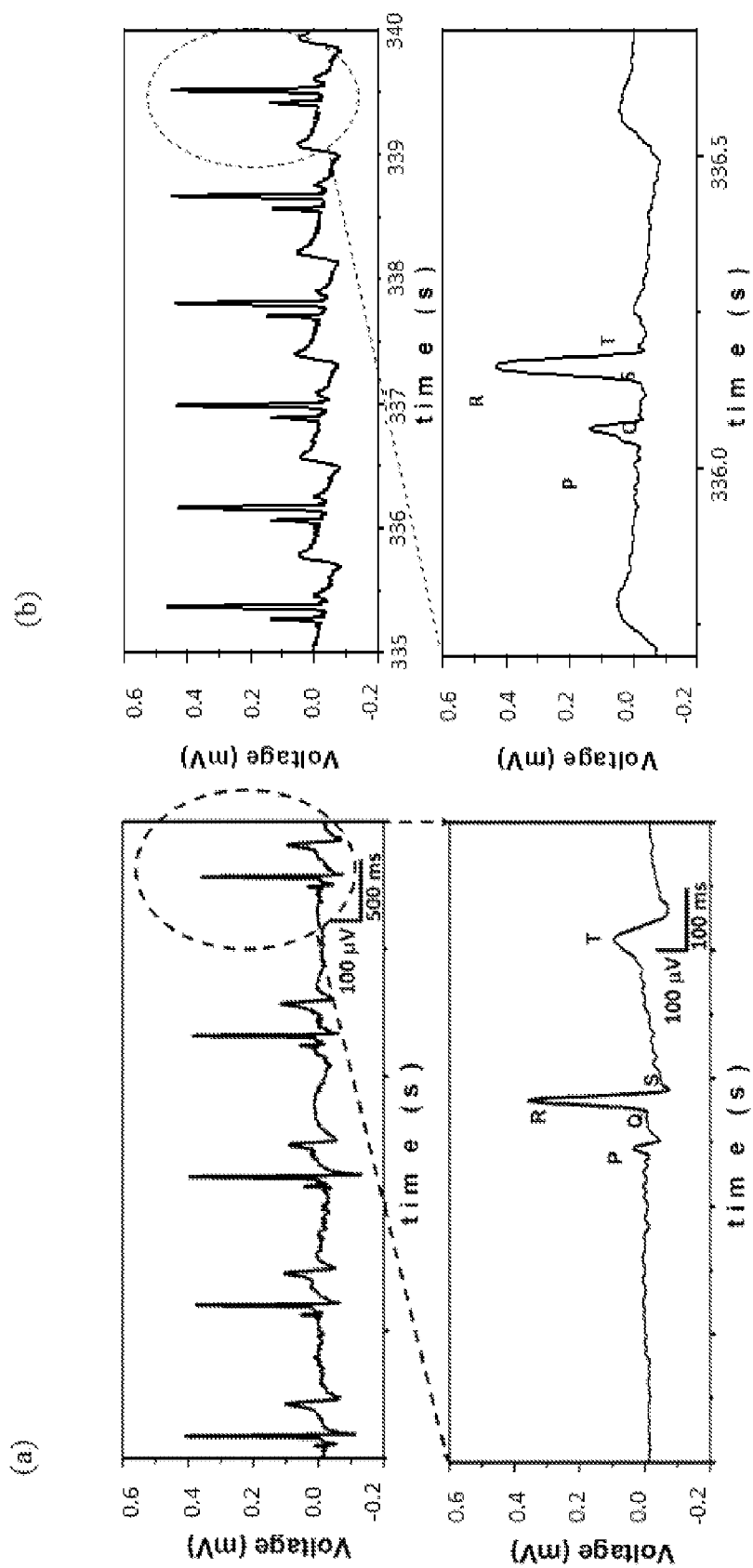

The (a) part in FIG. 6 is an electrocardiogram which is detected using the biological probe according to one embodiment of the present invention, and the (b) part in FIG. 6 is an electrocardiogram which is detected using the stainless steel biological probe.

DESCRIPTION OF THE PREFERRED EMBODIMENT

The present invention will be described in more detail in the following preferred embodiments taken in conjunction with the accompanying drawings. It is noted that the experiment data disclosed in the following embodiments is for convenience to explain the subject matters of the present invention, and it can never limit any aspects that can be embodied.

Figure 1:
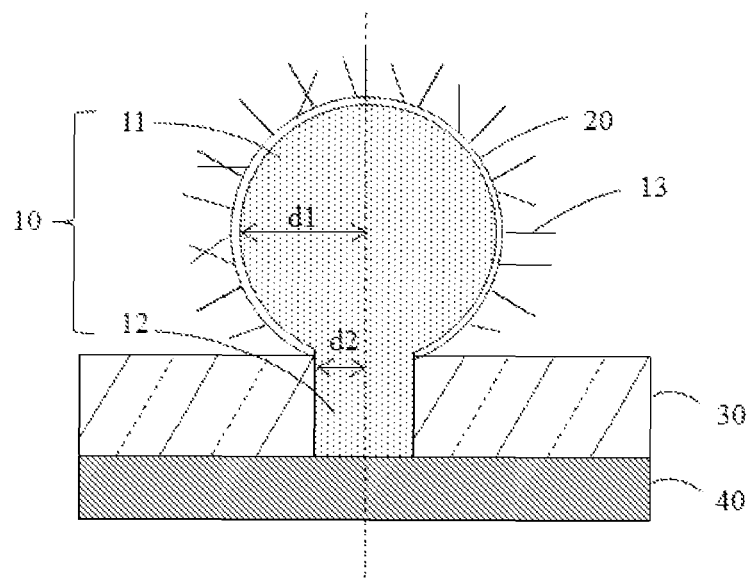
FIG. 1 is a sectional view of a three-dimensional electrode according to one embodiment of the present invention.

Please referring to FIG. 1, a three-dimensional electrode 10 with cell affinity and capacitive coupling according to one embodiment of the present invention comprises a spherical portion 11 and a pillar portion 12 connected to each other. An end of the three-dimensional electrode 10 is the spherical portion 11, and a radius of the spherical portion 11 is more than a radius of the pillar portion 12, which can effectively increase the surface area of the end of the electrode, and thus increase the capacitance and lower the impedance.

A material of the spherical portion 11 and the pillar portion 12 may be selected from one of a group consisted of gold, platinum, and titanium. Preferably, a material of the spherical portion 11 and the pillar portion 12 may be gold. Wherein, a radius d1 of the spherical portion 11 is more than a radius d2 of the pillar portion 12, and the radius of the spherical portion 11 may be in a range from about 0.1 μm to about 100 μm. Preferably, the radius of the spherical portion 11 may be in a range from about 0.1 μm to about 10 μm. A height of the pillar portion may be in a range from about 0.1 μm to about 100 μm. Preferably, the height of the pillar portion may be in a range from about 0.1 µm to about 10 µm. The height of the pillar portion may be more than, equal to or less than a diameter of the spherical portion 11.

The carbon nanotubes 13 are formed on the spherical portion 11. The carbon nanotubes 13 can comprise single-walled carbon nanotubes or multi-walled carbon nanotubes. As such, the carbon nanotubes 13 can be formed on the spherical portion of the three-dimensional electrode 10 by the methods comprising chemical vapor deposition method, transfer printing method, or spin-coating method, etc. The carbon nanotubes 13 may be activated via a surface modification process. As such, the carbon nanotubes 13 may be processed with ultraviolet ozone, so as to lower the impedance and increase the capacitance. It is noted that the surfaces of the carbon nanotubes 13 may undergo a hydrophilic process. For example, the surfaces of the carbon nanotubes 13 may be modified with hydroxyl, carboxyl or amino.

Figure 2:
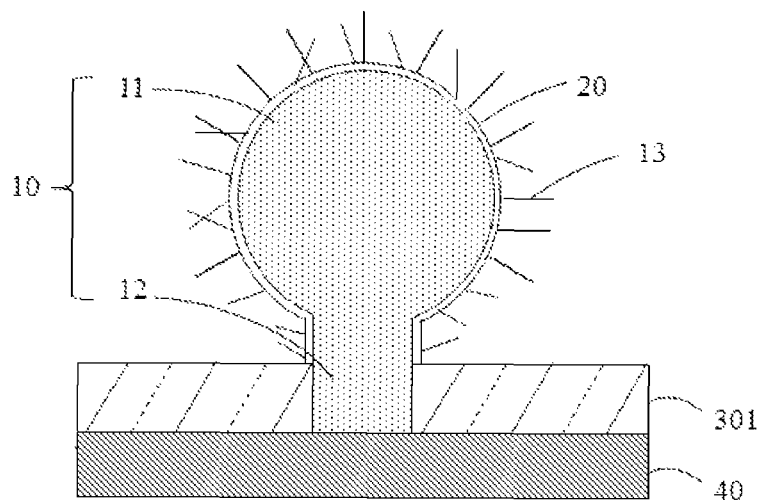
FIG. 2 is a sectional view of a three-dimensional electrode according to another embodiment of the present invention.
Figure 3:
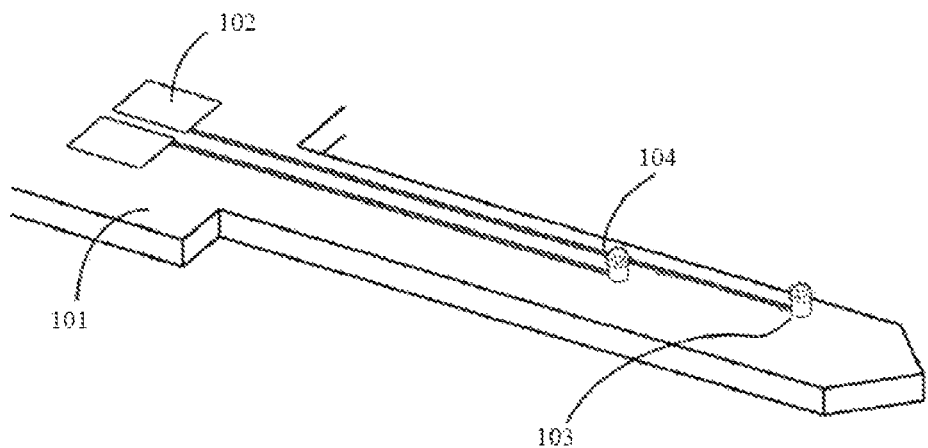
FIG. 3 is a schematic view of a biological probe according to one embodiment of the present invention.

The three-dimensional electrode 10 of the embodiment of the present invention is covered with a catalyst layer 20, and the carbon nanotubes 13 are formed on the catalyst layer 20. A material of the catalyst layer 20 may be selected from one of a group consisted of iron, cobalt and nickel. Preferably, the material of the catalyst layer 20 may be nickel. In one embodiment, the pillar portion 12 may comprise an insulating layer 30 disposed on its surface. That is, as shown in FIG. 1, the insulating layer 30 may completely cover the overall surface of the pillar portion 12. In another embodiment of the present invention, as shown in FIG. 2, an insulating layer 301 may partially cover the surface of the pillar portion 12. That is, a part of the pillar portion 12 is exposed beyond the insulating layer 301. As such, the catalyst layer 20 may be formed on a partial surface of the pillar portion 12, and the carbon nanotubes 13 may be formed on a partial surface of the pillar portion 12. The three-dimensional electrode 10 of the embodiment of the present invention may further comprise a conductive layer 40 disposed under the insulating layer.

The three-dimensional electrode of the present invention has superior impedance and capacitance properties, wherein the impedance of the three-dimensional electrode is less than 10 $\Omega/mm^2$, preferably less than 5 $\Omega/mm^2$, and most preferably less than 2 $\Omega/mm^2$. The capacitance of the three-dimensional electrode is more than 10 $mF/cm^2$, preferably more than 20 $mF/cm^2$, and most preferably more than 70 $mF/cm^2$.

According to another embodiment of the present invention, a biological probe 100 comprises: a base 101 which may be a silicon substrate or flexible substrate, e.g., polyamide (PI), parylene or polydimethylsiloxane (PDMS), but the above-mentioned materials are not a limitation; an output contact 102 disposed on the base 101; a three-dimensional electrode array 103 disposed on the base 101, the three-dimensional electrode array 103 being composed of the three-dimensional electrode 10 in the above-mentioned embodiment; and an interconnect conductive layer 104 disposed on the base 101 and electrically connecting the output contact 102 and the three-dimensional electrode array 103.

Figure 4A:
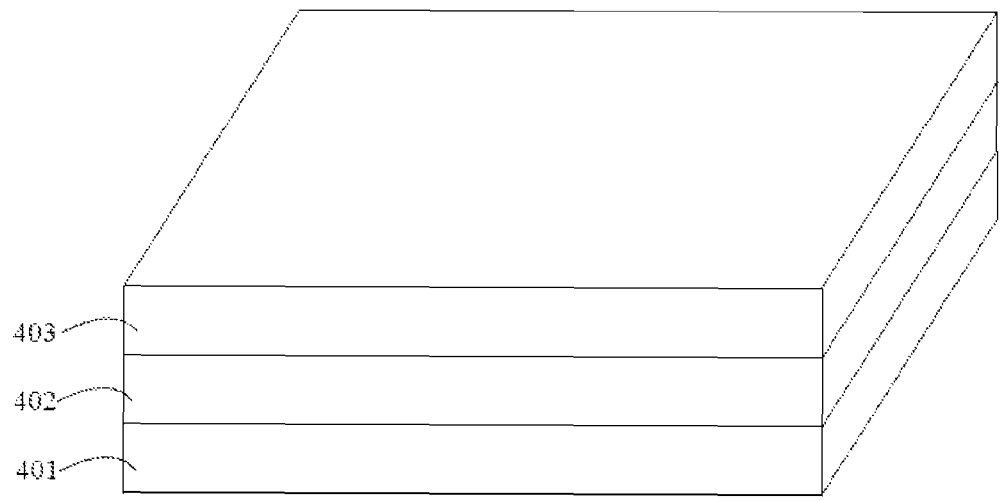
FIG. 4A through FIG. 4F are schematic views of a preparation method of the three-dimensional electrode according to one embodiment of the present invention.
Figure 4B:
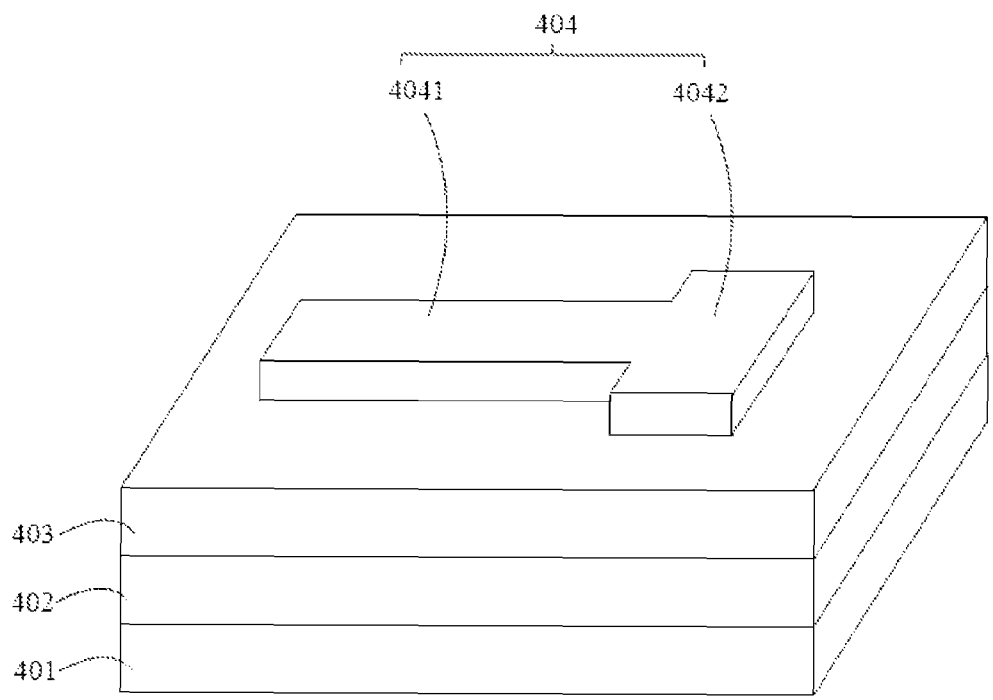
Figure 4C:
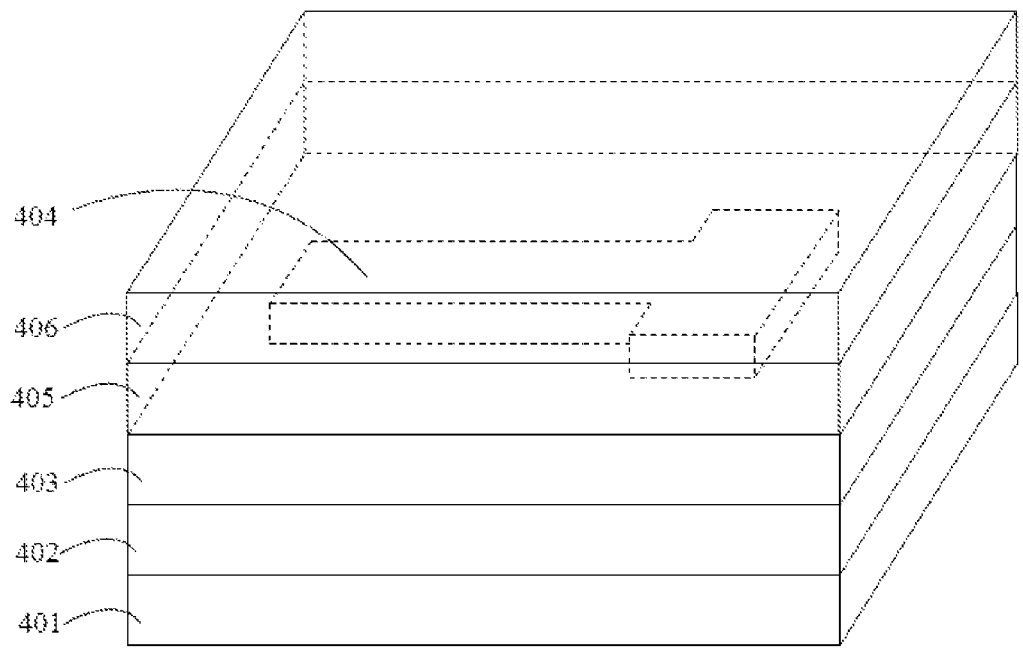
Figure 4D:
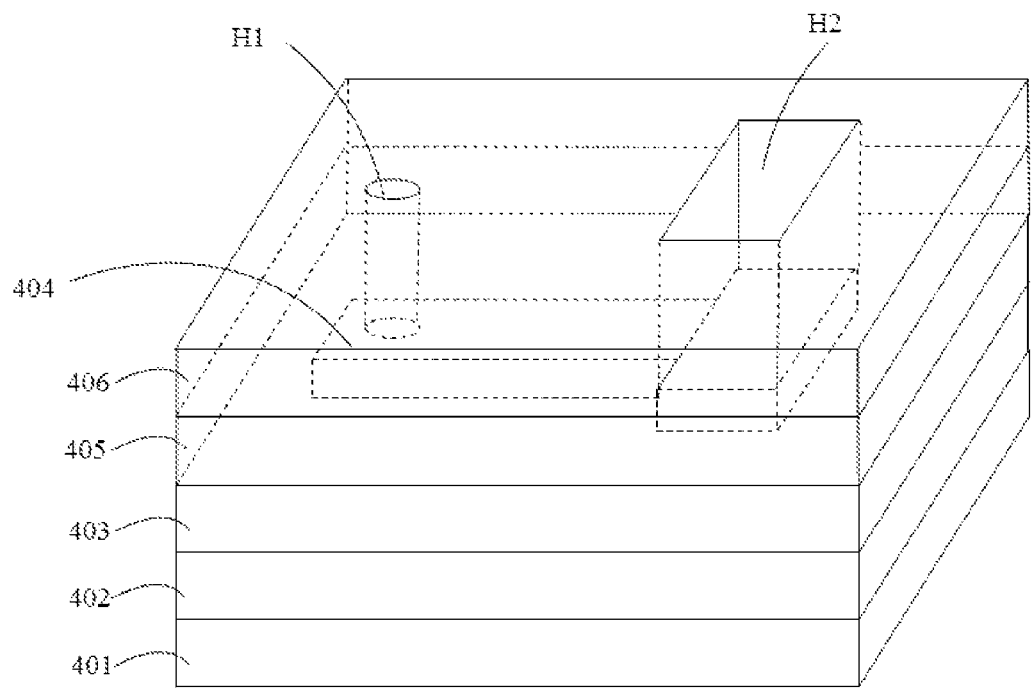

According to yet one embodiment of the present invention, a preparation method of the three-dimensional electrode of the present invention will be described in detail below in reference to FIG. 4A through FIG. 4F. First, a silicon oxide layer 402 is deposited on a silicon chip 401. For example, the deposition is performed with a plasma enhanced chemical vapor deposition method. Then, a photoresist layer 403 is spin-coated on the silicon oxide layer 402, as shown in FIG. 4A. Then, a conductive metal layer 404 is formed on the photoresist layer 403 with an electron beam physical vapor deposition method, wherein an interconnect conductive layer 4041 and an output contact 4042 are defined in the conductive metal layer 404 with a photolithography process, as shown in FIG. 4B. Subsequently, a silicon oxide layer 405 and a photoresist layer 406 are successively coated on the above-mentioned conductive metal layer 404, as shown in FIG. 4C. Then, a second photolithography process is performed to etch the silicon oxide layer 405, so as to produce openings H1, H2 for preparing the three-dimensional electrode, as shown in FIG. 4D.

Figure 4E:
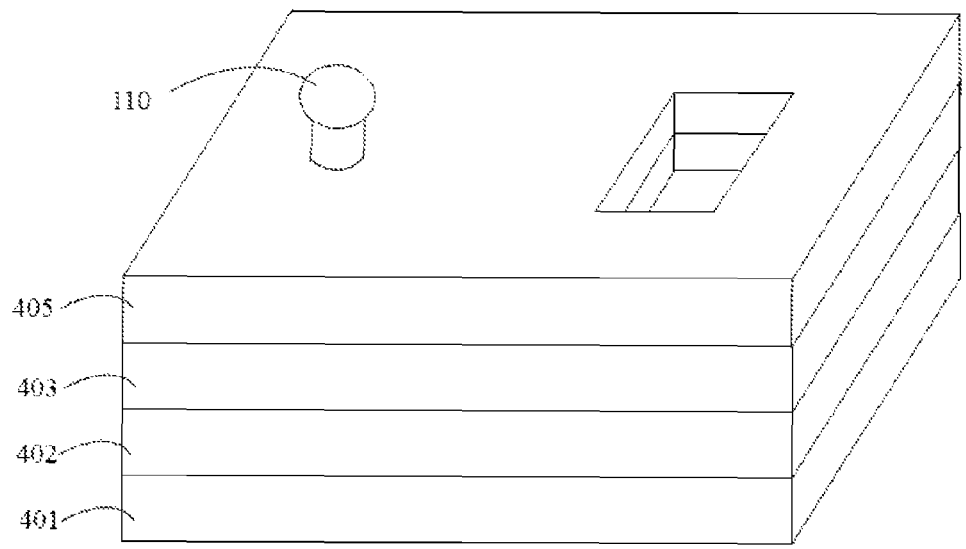
Figure 4F:
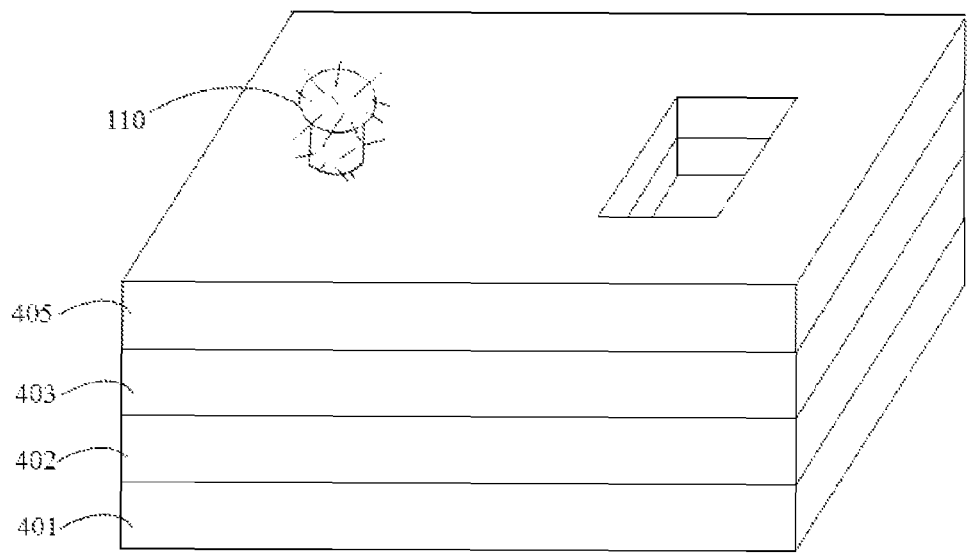

Referring to FIG. 4E, a golden three-dimensional electrode 110 is formed in the opening H1 by electroplating. In a preferred embodiment, a catalyst layer may be electroplated on the golden three-dimensional electrode 110. A material of the catalyst layer may be selected from one of a group consisted of iron, cobalt and nickel. Preferably, the material of the catalyst layer may be nickel. Finally, as shown in FIG. 4F, carbon nanotubes may be formed on the golden three-dimensional electrode 110 by a chemical vapor deposition method, a transfer printing method, or a spin-coating method, etc. The three-dimensional electrode of the present invention may be prepared by the above-mentioned steps.

Then, to detect the impedance and the capacitive coupling of the three-dimensional electrode of the present invention, tests will be performed on the following three sets of three-dimensional electrodes: (1) the golden three-dimensional electrode; (2) the golden three-dimensional electrode coated with carbon nanotubes (CNT-golden three-dimensional electrode); (3) the golden three-dimensional electrode coated with carbon nanotubes processed with ultraviolet ozone (UVo-CNT-golden three-dimensional electrode), i.e., the three-dimensional electrode of the embodiment of the present invention. Among them, the main structure of the electrodes of (1) and (2) are similar to that of the electrode of (3), and what is different is that the electrode of (1) is not coated with carbon nanotubes and the electrode of (2) is coated with carbon nanotubes which are not processed with ultraviolet ozone. The test results are as shown in FIG. 5.

Figure 5:
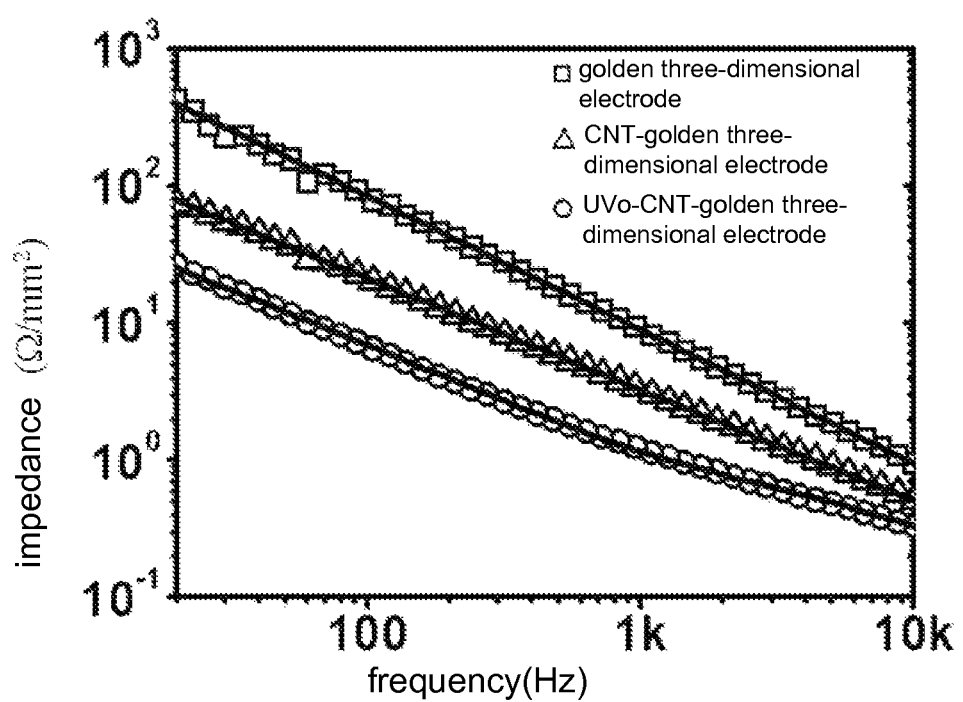
FIG. 5 is the test results of the impedance of various golden three-dimensional electrodes.

Referring to FIG. 5, it is discovered that the golden three-dimensional electrode coated with carbon nanotubes processed with ultraviolet ozone has a much lower impedance compared with the other two electrodes. The results are quantified as numeral, as shown in the following Table 1:

TABLE 1

| | impedance($\Omega/mm^2$)@1 kHz | capacitance($mF/cm^2$) |
|---|---|---|
| the golden three-dimensional electrode | 9.3 | 2.2 |
| CNT-golden three-dimensional electrode | 3.2 | 25.1 |
| UVo-CNT-golden three-dimensional electrode | 1.2 | 73.3 |

It is known from the above Table 1 that the golden three-dimensional electrode coated with carbon nanotubes may have a larger contact area between the electrode surface and the cells to be detected, compared with the golden three-dimensional electrode without coated with carbon nanotubes, so that the impedance can be lowered and the capacitance can be increased to improve capacitive coupling, and a preferred cell affinity may be obtained. However, when the carbon nanotubes on the golden three-dimensional electrode are further processed with ultraviolet ozone, a lower impedance (1.2 Ω/mm$^2$) and a larger capacitance (73.3 mF/cm$^2$) can be obtained, compared with the other two golden three-dimensional electrode.

In one illustrative embodiment, the probe having the three-dimensional electrode with cell affinity and capacitive coupling of the present invention may be used for heart signal detection as well. In this embodiment, the above-mentioned biological probe of the present invention and a stainless steel electrode probe are respectively used for detecting the heart signal of a zebrafish to obtain electrocardiograms, as shown in FIG. 6. The (a) part in FIG. 6 is an electrocardiogram of the heart of a zebrafish, which is detected using the above-mentioned biological probe of the present invention, and the (b) part in FIG. 6 is an electrocardiogram of the heart of a zebrafish, which is detected using the stainless steel electrode probe. It can be discovered that the electrocardiogram, which is detected using the above-mentioned biological probe of the present invention, may have a more complete T wave recorded. In general, the T wave of the electrocardiogram may reflect a voltage change of the ventricle during recovery after electrically-stimulated, which is an observation target of the detection of the ventricular re-polarization. Therefore, if a more detailed waveform is captured, a more correct judgment basis can be provided to a detector, so that the measurement results may have no distortion. The above-mentioned results are quantified as shown in Table 2.

TABLE 2

| | the biological probe of the present invention | the stainless steel electrode probe |
|---|---|---|
| average signal $V_{p-p}$ (μV) | 470.6 | 468.6 |
| noise $V_{rms}$ (μV) | 2.8 | 3.9 |
| T wave $V_{p-p}$ (μV) | 150.2 | 34.8 |

It is known from Table 2 that the above-mentioned biological probe of the present invention actually can be applied to the detection of the electrocardiogram, and a more detailed heart electrical signal can be obtained, compared with a conventional stainless steel probe.

To sum up the foregoing descriptions, the three-dimensional electrode with cell affinity and capacitive coupling of the present invention may be provided with preferred cell affinity, because the three-dimensional electrode of the present invention is doped with carbon nanotubes processed with ultraviolet ozone and has a larger contact area with the cells. In addition, the three-dimensional electrode of the present invention may be provided with a lower impedance and larger capacitive coupling, so that the three-dimensional electrode of the present invention can provide long-term and reliable signal detection, compared with the conventional three-dimensional electrode. Moreover, in addition to detect the electrical signals of the neural cells, the biological probe comprising the above-mentioned three-dimensional electrode can be more effectively applied to the detection of the electrocardiogram to provide more accurate and less distorted electrical signals and can provide the biomedical detection industry with more choices of a preferred biological probe.

The embodiments as above only illustrate the technical concepts and characteristics of the present invention; it is purposed for person ordinary skill in the art to understand and implement the present invention, but not for the limitation to claims of the present invention. That is, any equivalent change or modification in accordance with the spirit of the present invention should be covered by the appended claims.

What is claimed is:

1. A three-dimensional electrode with cell affinity and capacitive coupling, comprising:
a pillar portion and a spherical portion connected to each other, wherein a radius of the spherical portion is greater than a radius of the pillar portion, carbon nanotubes are formed on the the spherical portion and the pillar portion and the spherical portion are made of a metal material.

2. The three-dimensional electrode with cell affinity and capacitive coupling according to claim 1, wherein the pillar portion and the spherical portion are made of gold, platinum or titanium.

3. The three-dimensional electrode with cell affinity and capacitive coupling according to claim 1, wherein the radius of the spherical portion ranges from about 0.1 μm to about 100 μm.

4. The three-dimensional electrode with cell affinity and capacitive coupling according to claim 1, wherein a height of the pillar portion ranges from about 0.1 μm to about 100 μm.

5. The three-dimensional electrode with cell affinity and capacitive coupling according to claim 1, having an impedance less than 10 Ω/mm2.

6. The three-dimensional electrode with cell affinity and capacitive coupling according to claim 1, having a capacitance more than 10 mF/cm2.

7. The three-dimensional electrode with cell affinity and capacitive coupling according to claim 1, wherein the pillar portion further comprises an insulating layer configured to at least cover partially the surface of the pillar portion.

8. The three-dimensional electrode with cell affinity and capacitive coupling according to claim 7, wherein the carbon nanotubes are formed on a surface of the pillar portion which is not covered by the insulating layer.

9. The three-dimensional electrode with cell affinity and capacitive coupling according to claim 1, wherein surfaces of the carbon nanotubes are modified with hydroxyl, carboxyl or amino group.

10. A biological probe, comprising:
a base;
an output contact disposed on the base;
a three-dimensional electrode array disposed on the base, the three-dimensional electrode array being composed of a three-dimensional electrode with cell affinity and capacitive coupling; and
an interconnect conductive layer disposed on the base and electrically connecting the output contact and the three-dimensional electrode array;
wherein the three-dimensional electrode with cell affinity and capacitive coupling comprising:
a pillar portion and a spherical portion connected to each other, wherein a radius of the spherical portion is greater than a radius of the pillar portion, carbon nanotubes are formed on the spherical portion and the pillar portion and the spherical portion are made of a metal material.

11. The biological probe according to claim 10, wherein the pillar portion and the spherical portion are made of gold, platimum, or titanium.

12. The biological probe according to claim 10, wherein the radius of the spherical portion ranges from about 0.1 μm to about 100 μm.

13. The biological probe according to claim 10, wherein a height of the pillar portion ranges from about 0.1 μm to about 100 μm.

14. The biological probe according to claim 10, wherein the three-dimensional electrode with cell affinity and capacitive coupling having an impedance less than 10 Ω/mm2.

15. The biological probe according to claim 10, wherein the three-dimensional electrode with cell affinity and capacitive coupling having a capacitance more than 10 mF/cm2.

16. The biological probe according to claim 10, wherein the pillar portion further comprises an insulating layer configured to at least cover partially the surface of the pillar portion.

17. The biological probe according to claim 16, wherein the carbon nanotubes are formed on a surface of the pillar portion which is not covered by the insulating layer.

18. The biological probe according to claim 10, wherein surfaces of the carbon nanotubes are modified with hydroxyl, carboxyl or amino group.

* * * * *